United States Patent [19]

Lackey

[11] Patent Number: 5,053,037
[45] Date of Patent: Oct. 1, 1991

[54] FEMORAL INSTRUMENTATION FOR LONG STEM SURGERY

[75] Inventor: Jennifer J. Lackey, Memphis, Tenn.

[73] Assignee: Smith & Nephew Richards Inc., Memphis, Tenn.

[21] Appl. No.: 666,262

[22] Filed: Mar. 7, 1991

[51] Int. Cl.⁵ .................................................. A61F 5/04
[52] U.S. Cl. .......................................... 606/79; 606/80; 606/88; 606/96
[58] Field of Search ....................... 606/80, 88, 62, 79, 606/96, 63, 64, 65, 67, 98, 97

[56] References Cited

U.S. PATENT DOCUMENTS

| | | | |
|---|---|---|---|
| 4,467,801 | 8/1984 | Whiteside | 606/88 |
| 4,474,177 | 10/1984 | Whiteside | 606/88 |
| 4,487,203 | 12/1984 | Androphy | 606/88 |
| 4,567,885 | 2/1986 | Androphy | 606/88 |
| 4,567,886 | 2/1986 | Petersen | 606/88 |
| 4,721,104 | 1/1988 | Kaufman | 606/88 |
| 4,773,407 | 9/1988 | Petersen | 606/88 |
| 4,892,093 | 1/1990 | Zarnowski | 606/88 |
| 4,926,847 | 5/1990 | Luckman | 606/88 |

*Primary Examiner*—Mickey Yu
*Assistant Examiner*—Michael Brown
*Attorney, Agent, or Firm*—Pravel, Gambrell, Hewitt, Kimball & Krieger

[57] ABSTRACT

Improved femoral instrumentation for long stem surgery provides a femoral drill guide with interchangeable femoral collets, a femoral reamer, and a femoral anterior/posterior cutting block with an adaptable anterior femoral ledge. This instrumentation allows all cuts to be made relative to the long stem component of a femoral prosthesis which will fit in the hole formed by the reamer with the collet and cutting block both oriented on the reamer, and all cuts made by the surgeon will be oriented relative to the long stem or spike component of the femoral prosthesis.

25 Claims, 6 Drawing Sheets

FEMORAL INSTRUMENTATION FOR LONG STEM SURGERY

BACKGROUND OF THE INVENTION

1. Field of the Invention

The present invention relates to femoral instrumentation, more particularly relates to improved femoral instrumentation for long stem surgery utilizing a femoral drill guide with interchangeable femoral collets, a femoral reamer, and a femoral anterior/posterior cutting block with an adaptable anterior femoral ledge. This instrumentation allows all cuts to be made relative to the long stem component of a femoral prosthesis which will fit in the hole formed by the reamer with the collet and cutting block both oriented on the reamer, all cuts made by the surgeon will be oriented relative to the long stem or spike component of the femoral prosthesis.

Even more particularly, the present invention relates to femoral instrumentation for long stem surgery used in knee surgery where a femoral long stemmed component is needed for fixation and/or support and instrumentation of the present method and apparatus is used to correctly orient the femoral long stem hole and the femoral cuts by referencing off the existing anterior femoral cortex or other existing reference points (e.g., epicondyles). The instruments also ensure appropriate positioning to prevent anterior femoral notching.

2. General Background

Often a knee prosthesis must be replaced, referred to as a revision case. In revision surgery, the existing femoral component is removed from the distal femur. If cement was the means of attachment, it is cleaned and removed from the femur. The distal femur must then be recut. In severe primary cases, the distal femur is also cut appropriately.

Various devices have been patented which relate to the resectioning and preparation of the distal femur for prosthetic devices. In U.S. Pat. No. 4,474,177, entitled "Method and Apparatus For Shaping A Distal Femoral Surface", there is disclosed a method and apparatus for resectioning of the distal femur. An intramedullary reamer is used to internally locate the central longitudinal axis of the femur. The reamer is then removed and an intramedullary alignment guide is inserted in its place. The alignment guide has a handle attached to a rod portion at a preselected angle. Femoral surface modifying instruments can then be fixed to the guide handle and thus assume proper alignment with respect to the central longitudinal axis of the femur.

In U.S. Pat. No. 4,567,885, entitled "Triplanar Knee Resection System", there is provided a system for preparing a knee joint for a prosthesis. The triplanar system includes a guide member which has three pairs of parallel slots. The system further includes an intramedullary guide rod which is inserted into the femur. The guide rod has a 90° bend. The guide member is affixed to the guide rod, the guide rod being used as an alignment means for the guide member. This patent is a divisional of U.S. Pat. No. 4,487,203, issued Dec. 11, 1984.

U.S. Pat. No. 4,722,330, entitled "Femoral Surface Shaping Guide For Knee Implants", discloses a distal femoral surface shaping guide for mounting on an intramedullary alignment guide. The main body of the shaping guide preferably contains at least one shaping guide surface. It may have an attachment for other shaping guides, however, preferably the main body of the shaping guide has integrally formed shaping guide surfaces.

U.S. Pat. No. 4,791,919, entitled "Surgical Instruments", discloses a set of femoral instruments which includes a femoral intramedullary alignment rod which may be introduced into the medulla by an alignment rod introducer. An angle adaptor which slides over the alignment rod forms a basis for the preparation of the femur using saw guides to receive the femoral component of the knee prosthesis.

U.S. Pat. No. 4,703,751, entitled "Method And Apparatus For Resecting A Distal Femoral Surface". The '751 patent discloses a method and apparatus for resecting a distal femoral surface. The apparatus includes an intramedullary rod, a jig which attaches to the rod, a cutting plate and a reference bar. The method and apparatus disclosed are for forming the initial resection along the transverse axis.

U.S. Pat. No. 4,738,254, entitle "Positioner For Surgical Instruments", discloses a positioner for surgical instruments used to invade a bone. The positioner comprises a body means, an alignment plate, and an alignment rod. The body has at least one guide surface for positioning a resectioning surgical instrument. The alignment rod which extends into the femoral shaft is used to locate the main body of the femoral resection guide in the correct position.

In U.S. Pat. No. 4,759,350, there is disclosed an apparatus and system for preparing distal femur and proximal tibia ends to receive a knee prosthesis. An intramedullary alignment guide is used to reference a femoral alignment guide for attachment across the distal femur after the distal femur cut has been made. The femoral alignment guide is in turn a reference for several cutting guides.

U.S. Pat. No. 4,907,578, discloses a distal femoral resector for resecting the distal femur. The resector comprises a T-shaped base with a rotating rod mounted through the base and an intramedullary alignment rod. The resector has a guide slot for guiding a cutting tool.

In U.S. Pat. No. 4,935,023, there is disclosed a distal femoral surface shaping guide which is mounted on an intramedullary alignment rod. The apparatus and method disclosed are particularly suitable for shaping one condyle for attachment of a unicondylar prosthesis.

SUMMARY OF THE INVENTION

The present invention provides femoral instrumentation for long stem surgery. The present invention provides a number of instruments and a method for femoral instrumentation for long stem surgery. The instruments will be used in knee surgery where a femoral long stemmed component is needed for fixation and/or support. The instruments include a femoral drill guide, a femoral collet, a femoral reamer, a femoral anterior/posterior cutting block and an adaptable anterior femoral ledge. The instruments are used to correctly orient the femoral long stem hole and the femoral cuts off the existing anterior femoral cortex to ensure appropriate positioning and to prevent anterior femoral notching. If it is a revision surgery, the existing femoral component is removed from the distal femur. If cement was the means of attachment, it is cleaned and removed from the femur. Then the distal femur is recut, if needed. If the apparatus and method of the present invention are used in a severe primary case, the distal femur is cut appropriately.

After the distal femoral cut is completed, the correct size femoral drill guide is chosen by determining which guide fits best in the anterior/posterior and medial/lateral dimensions to ensure equal flexion and extension spaces. The femoral drill guide is positioned on the distal femur by placing the anterior ledge on the existing anterior femoral cortex.

Once correct medial/lateral and rotational orientation is achieved, the femoral drill guide is affixed to the femur anteriorly and/or medial/laterally by means of at least one pin or drill bit through the anterior ledge or through the attachable handle. The appropriate size femoral collet is attached to the femoral drill guide and positioned for a left or right knee.

The matching sized femoral reamer is then inserted through the femoral collet and is advanced into the intramedullary canal. The femoral reamer can be calibrated to determine how deep into the canal the reamer has advanced. Femoral lug holes can be drilled, if needed, through the femoral drill guide. When reaming and drilling is complete, the femoral drill guide is removed from the femur and the femoral reamer is left in place in the intramedullary canal.

The same size revision femoral anterior/posterior (A/P) cutting block is then attached to the intramedullary reamer. If the femoral lug holes have been drilled to accept the revision femoral A/P cutting block studs, the studs can then be placed into the holes for correct rotation orientation. If there is little or no femoral bone to affix the femoral anterior/posterior cutting block studs in, then the adaptable anterior femoral ledge can be attached to the cutting block. The correct rotation can be determined and the femoral anterior/posterior cutting block can be affixed to the anterior and/or medial/lateral femur by inserting at least one pin or drill bit through the adaptable anterior femoral ledge or the attachable handle. The anterior/posterior, and the anterior/posterior chamfer cuts can then be made through or over the femoral anterior/posterior cutting block.

If needed, the femoral drill guide can be reattached to the distal femur in the same manner as stated above and larger sized femoral collets can be positioned to ream for larger femoral stems.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
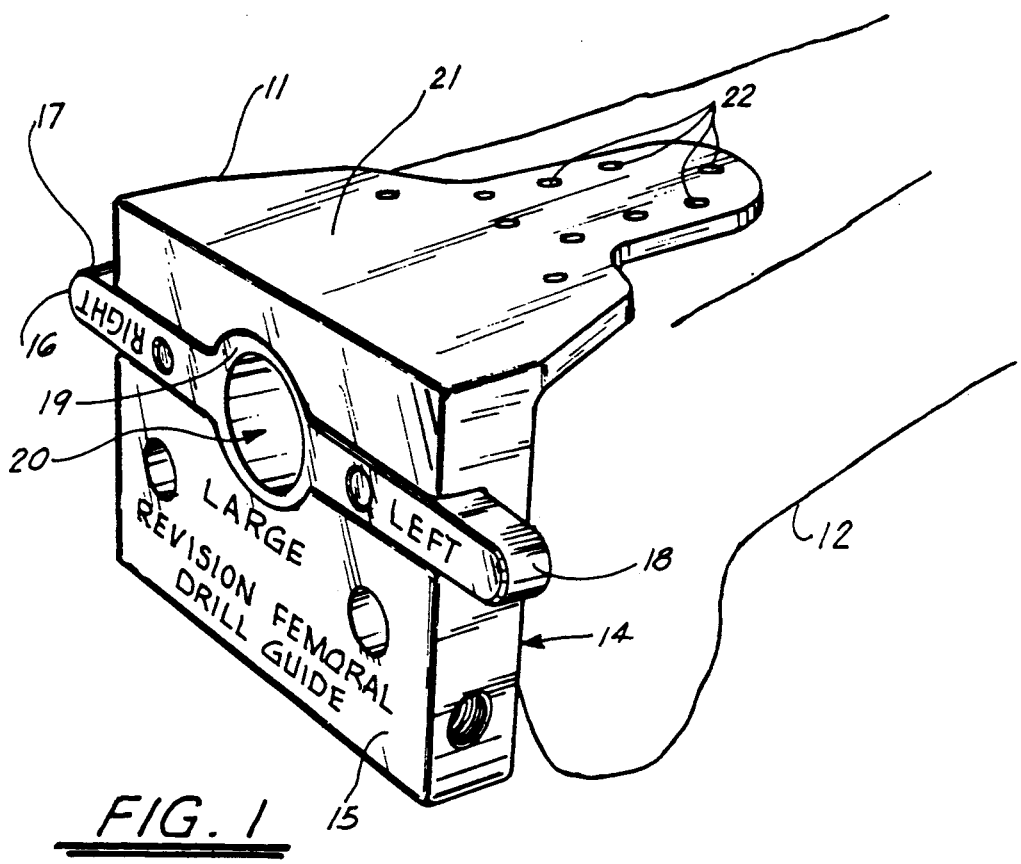
FIG. 1 is a partial perspective view of the preferred embodiment of the apparatus of the present invention illustrating the femoral drill guide portion thereof with collet attached.

The femoral instrumentation apparatus of the present invention includes a femoral drill guide body 11 (FIG. 1) adapted for placement during use on the distal femur 12. The drill guide 11 includes a generally rectangular portion 13 having a flat under 14 surface that orients upon the end of the distal femur 12A and a flat 15 top surface portion that accommodates removable collet 16. Collet 16 includes a pair of spaced apart handles 17, 18 and a central portion 19 having a cylindrical opening 20 therethrough which is angularly oriented with respect to flat surfaces 14, 15. This angular orientation of opening 20 accommodates for the difference between the anatomical axis of the femoral intramedullary canal 12B and the mechanical axis which is defined by a line that passes through the center of the femoral head and the midline of the knee joint and ankle joint. The end of the distal femur is designated by the numeral 12A in FIG. 13.

Figure 2:
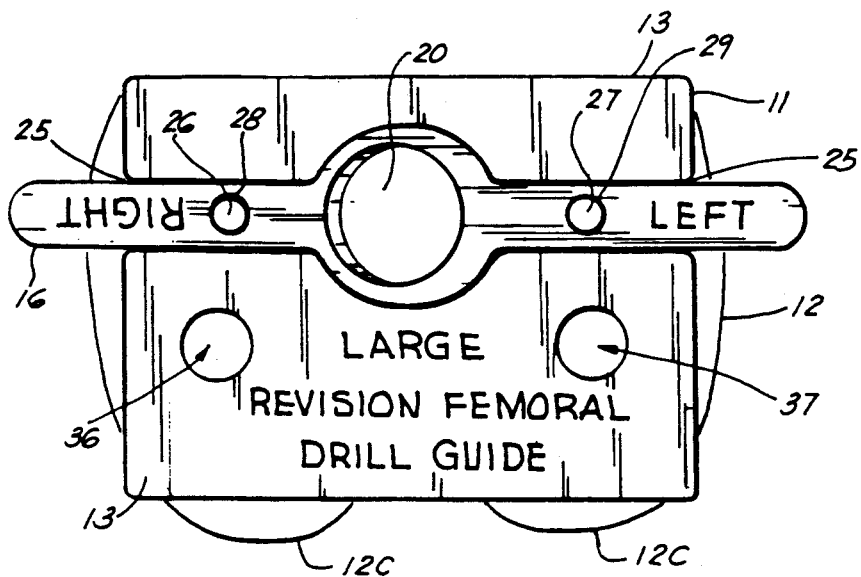
FIG. 2 is a partial end view of the preferred embodiment of the apparatus of the present invention illustrating the femoral drill guide portion thereof with the collet attached.
Figure 3:
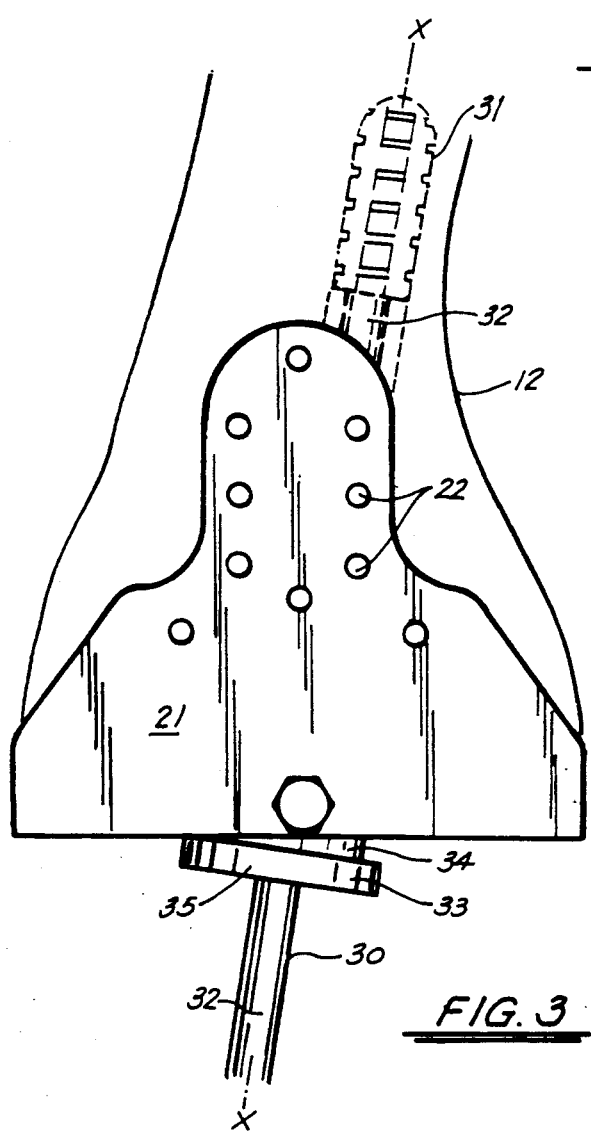
FIG. 3 is a partial schematic anterior view of the preferred embodiment of the apparatus of the present invention illustrating the femoral drill guide portion with the reamer/drill in an operative position.

In FIGS. 2 and 3, the drill guide 11 is shown in an end view and in a anterior view respectively upon femur 12. In FIG. 2, the posterior condyles 12C of the femur 12 can be shown extending beyond the bottom rectangular drill guide body 13. Removable collet 16 attaches to guide body 11 at an elongated slot 25 that extends transversely across the rectangular 13 portion of guide body 11. Slot 25 is shaped to receive collet 16. A pair of attachment posts 26, 27 receive collet 16 thereon. Collet 16 includes openings 28, 29 that register upon posts 26, 27. The posts 26, 27 can each be provided with a spring locking detent, such as a spring loaded ball, for example, to frictionally engage the collet 16 at the openings 28, 29.

An anterior ledge 21 provides a plurality of openings 22 that define drill or pin openings for preventing rotational and translational movement of the drill guide 11 with respect to femur 12. The anterior ledge 21 preferably provides a plurality of, for example, ten (10) openings 22 as shown in FIGS. 1 and 3. The surgeon can select any particular opening 22 for the placement of a pin or drill therethrough into the underlying femur for purposes of rigidifying the drill guide 11 and preventing rotation and translation.

Figure 4:
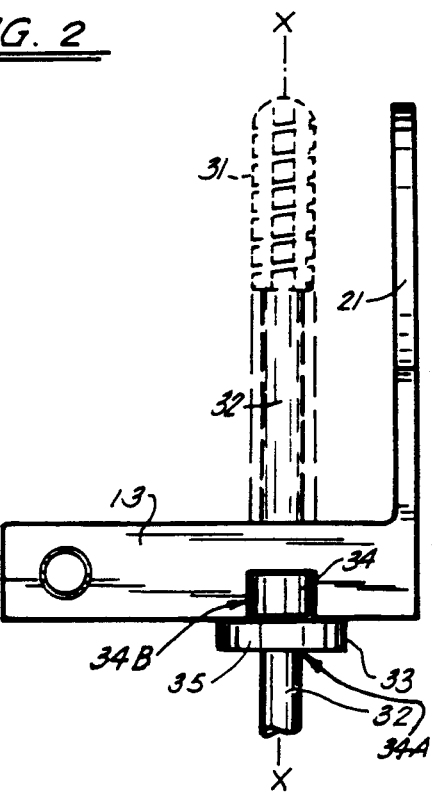
FIG. 4 is a partial side or lateral/medial view of the preferred embodiment of the apparatus of the present invention illustrating the drill guide portion with the reamer/drill in an operative position.

In FIGS. 3-4, there can be seen an elongated drill/reamer 30 having a lower cutting 31 portion and a smaller diameter shaft 32 portion, a drill/reamer sleeve 33 manufactured of plastic, for example, provides an inside diameter cylindrical portion 34A and an outside diameter cylindrical portion 34B, and a larger diameter cylindrical portion 35 in the form of an enlarged collar. The inside cylindrical portion 34 is sized to accept and centralize the drill/reamer shaft diameter 32. The cylindrical portion 34 is sized to snugly fit and centralize in opening 20 of collet 16, as shown in FIGS. 3 and 4. The axis X—X of drill/reamer 30 is shown in FIG. 3 as being angled with respect to a line normal to the flat upper surface 15 and the flat under surface 14 of drill guide portion 13. The flat surfaces 14, 15 are preferably flat plane, and/or parallel to one another.

In the preferred embodiment, the angle formed by the drill/reamer 30 with respect to a line normal to surfaces 14, 15 is on the order of zero–twenty degrees (0°-20°) but preferably five–eleven degrees (5°-20°) which accommodates the large majority of anatomical situations. The collets 16 are removable and thus each collet provides an opening 20 having a different angular orientation. Further, the collets can be provided with openings 20 of different cylindrical diameter such as 8 millimeters, 9 millimeters, etc. Thus, the removable collets 16 provide an adjustability both with regard to the angle of orientation of the drill/reamer 30 and also with regard to the diameter of drills/reamers that can be used based upon the selection of the diameter of opening 20 and of the size of sleeve 33.

The collet 16 are preferably reversible, as shown in FIGS. 1 and 2, having left and right sides for accommodating left and right femurs. The surgeon simply selects the proper collet position so as to orient the opening 20 in the direction that will correctly track the intramedullary canal with the reamer/drill 30.

The drill guide 11 main rectangular body 13 has a pair of openings 36, 37 which are sized based upon the anchoring pins of the femoral knee component and located with respect to the long stem of the femoral component.

Figures 5, 6, 7:
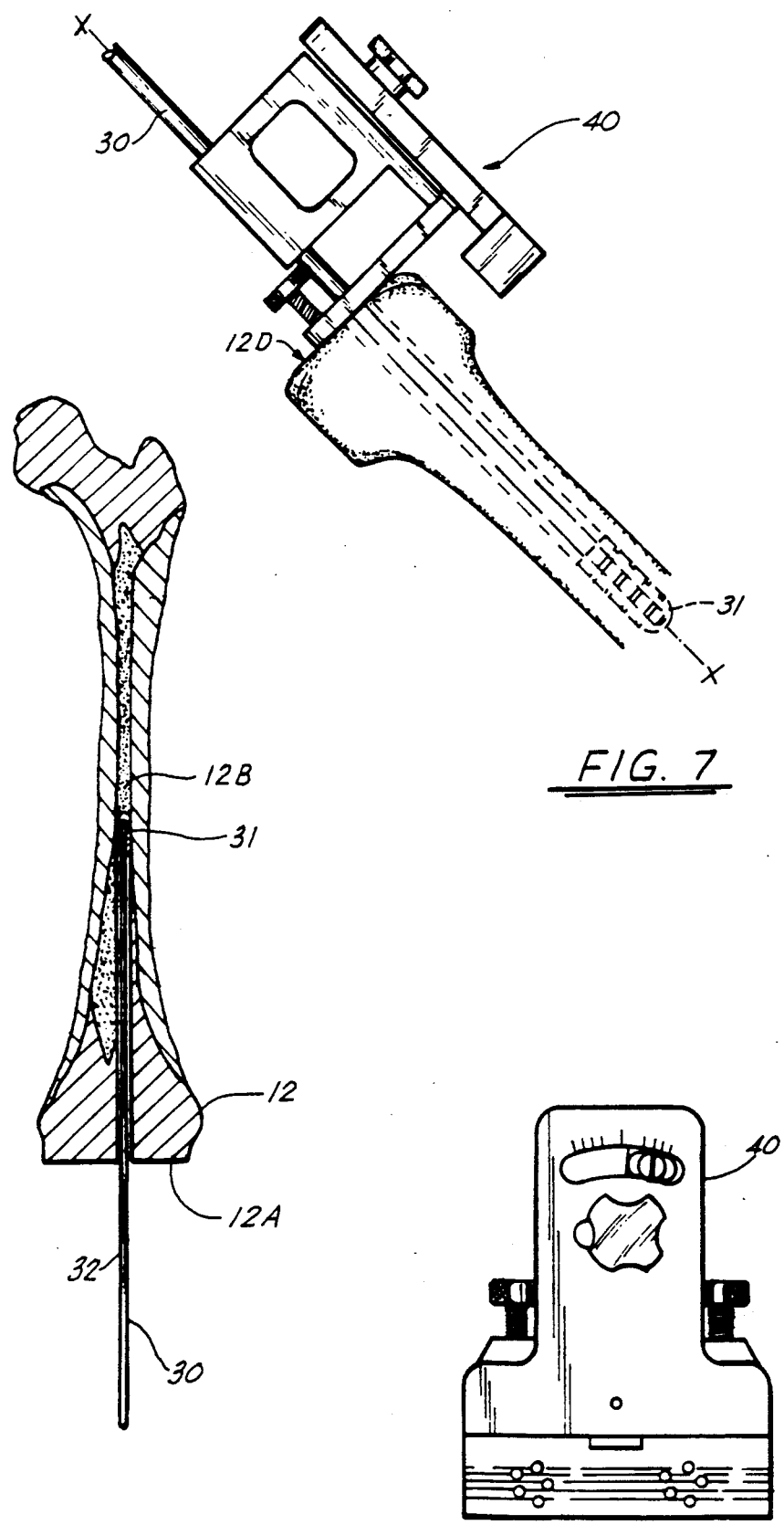
FIG. 5 is a partial side, schematic view of the preferred embodiment of the apparatus of the present invention illustrating the reamer/drill in an installed operative position within the intramedullary canal.
FIG. 6 is a top view of an alignment assembly/cutting block that can be used with the method of the present invention.
FIG. 7 is a side view or lateral/medial view of an alignment assembly/cutting block as aligned upon the drill/reamer as part of the method of the present invention.

FIGS. 5-10 illustrate the use of the femoral drill/reamer to orient a commercially available alignment guide. In FIG. 5, the femur 12 is illustrated with the flat distal end 12A in a revision case being shown. The drill/reamer 30 has been installed with the cutting 31 portion penetrating the intramedullary canal 12B. At this point, the drill/reamer 30 provides orientation for the alignment guide designated generally by the numeral 40 and thereafter, for the cutting block 50 portion of the present invention (see FIGS. 11-13).

Figure 8:
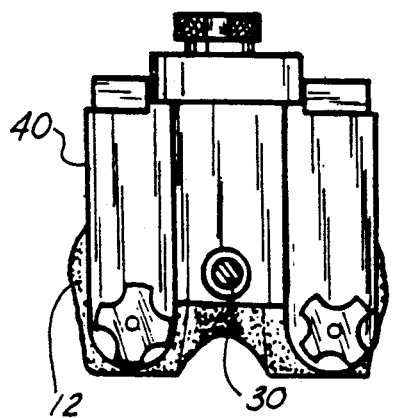
FIG. 8 is a end view of an alignment assembly/cutting block as aligned upon the drill/reamer as part of the method of the present invention.
Figure 9:
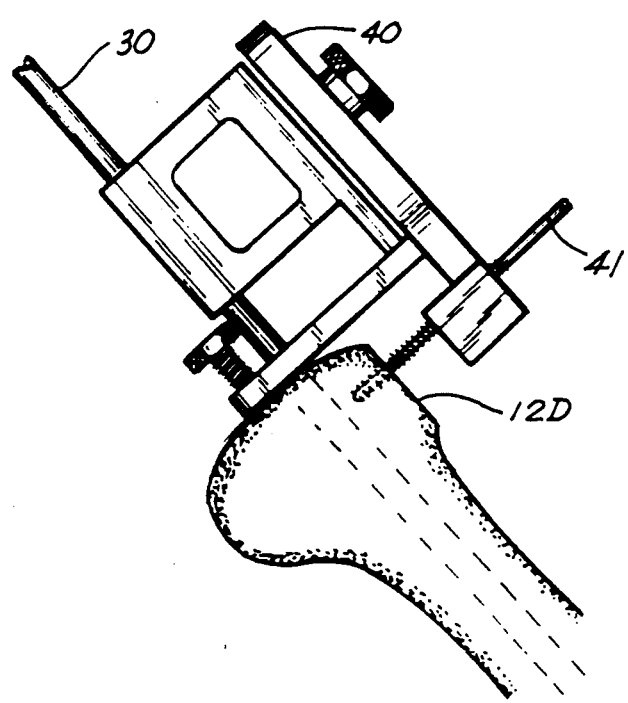
FIG. 9 is a side view of an alignment assembly/cutting block as aligned upon the drill/reamer as part of the method of the present invention.

FIG. 6 shows a top view of the alignment guide, whereas in FIG. 7, a side view is shown with the alignment guide positioned upon the drill/reamer and the top 12A of the distal femur. In FIG. 8 and 9, the proper orientation of the alignment guide 40 with femur 12 is shown, and upon drill/reamer 30 whereas FIG. 9 illustrates a side view thereof. A drill or pin 41 is illustrated in FIG. 9 as entering the anterior femur surface 12B.

Figure 10:
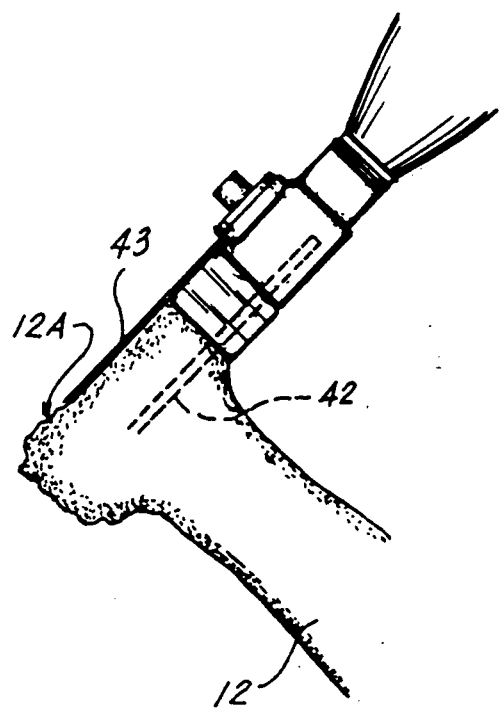
FIG. 10 is a side view or lateral/medial view of the femur illustrating a cutting of the distal femur as part of the method of the present invention.

The opening 42 formed by drill or pin 41 is shown in FIG. 10 wherein a blade 43 is used to dress the end of the distal femur 12A before attachment of the cutting block 50 thereto. It should be understood that the alignment guide illustrated in FIGS. 6-10 is a commercially available device sold by Smith & Nephew Richards Inc. of Memphis, Tenn. The alignment guide 40 is shown simply to illustrate how the drill/reamer 30 is used for orientation of the alignment guide 40 and also the cutting block 50 thereon after the drill/reamer 30 is installed using the femoral drill guide 11.

Figure 13:
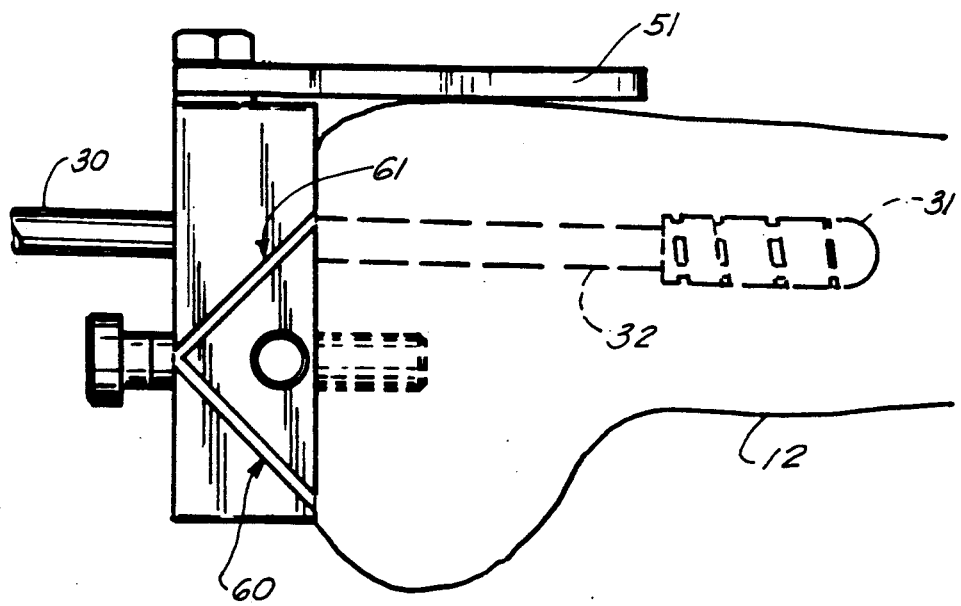
FIG. 13 is another partial side view of the preferred embodiment of the apparatus of the present invention illustrating the medial/lateral distal femur with revision anterior/posterior cutting block and anterior ledge adapter portions attached to the drill/reamer.
Figure 11:
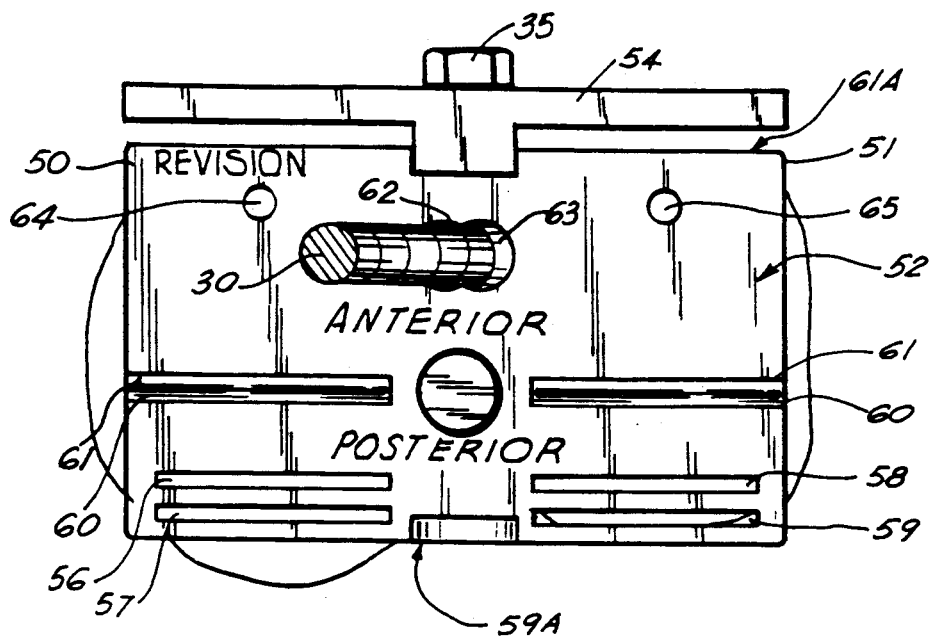
FIG. 11 is a partial end view of the preferred embodiment of the apparatus of the present invention illustrating the distal femur with revision anterior/posterior cutting block portion attached to the drill/reamer.
Figure 12:
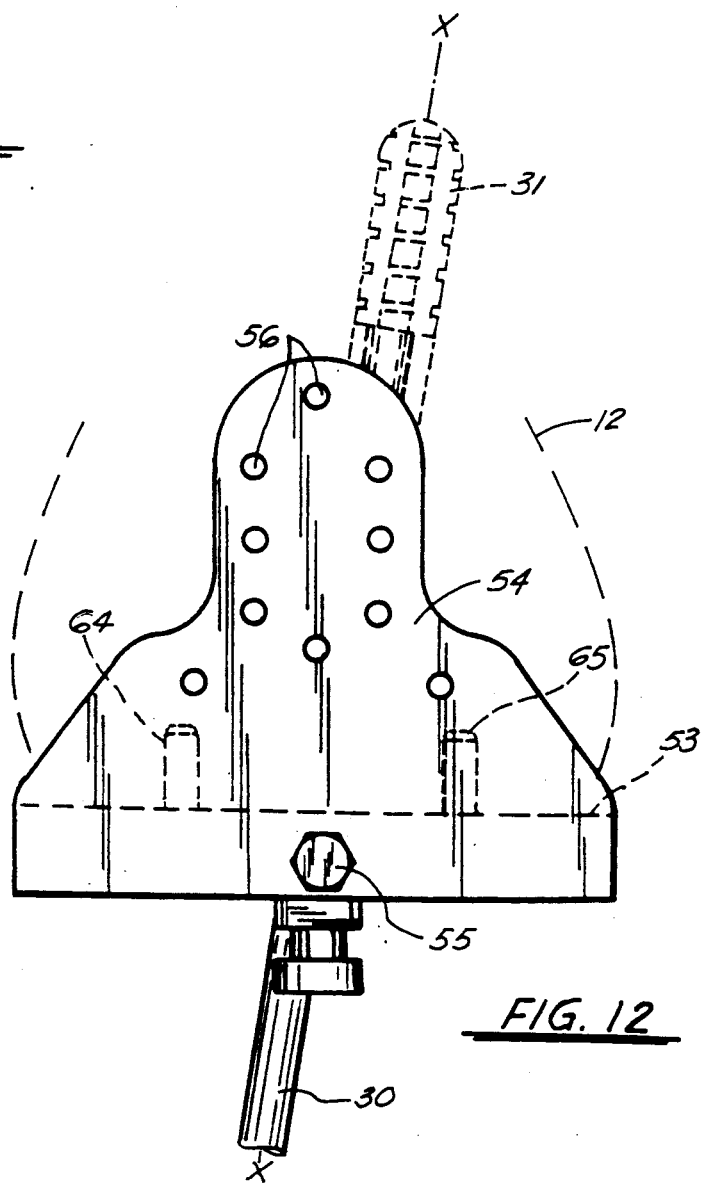
FIG. 12 is a partial view of the preferred embodiment of the apparatus of the present invention illustrating the anterior distal femur with revision anterior/posterior cutting block and anterior ledge adapter portions attached to the drill/reamer.

In FIGS. 11-13, the revision femoral anterior/posterior cutting block 50 is shown, comprising a generally rectangular cutting block portion 51 having an upper generally flat surface 52 and a lower flat surface 53 with an anterior ledge 54 being removably attached at bolted connection 55. The anterior ledge 54 can be shaped correspondingly to the ledge 21 of femoral drill guide 11, having the same plurality of openings to accommodate a drill or pin as the openings 22 of anterior ledge 21. Thus, the plurality of openings 56 in anterior ledge 54 can be correspondingly placed to the plurality of openings 22 in anterior ledge 21 of drill guide 11.

The cutting block 50 provides a plurality of guide slots 56-59 and guide surface 59A which are parallel and which accommodate a cutting blade for making posterior femoral cuts. The guide surface 61A accommodates a cutting blade to make the anterior femoral cut. A plurality of diagonal slots 60, 61 (FIG. 13) are provided for making diagonal cuts to the distal end of femur 12 when the cutting block 50 is positioned, as shown in FIG. 13. The cutting block 50 is preferably provided with a pair of permanent angled openings 62, 63, (or openings carried in collets) each of which is angled by a measure equal to the anatomical offset of the intramedullary canal as defined by the position of the drill/reamer 30 when occupying the intramedullary canal of the femur. The surgeon simply selects the degree of orientation of the cutting block 50 for a given anatomical offset by selecting from a plurality of cutting blocks 50, or by means of removable collets. The cutting block 50 can provide a pair of spaced apart pegs 64, 65 that register in cavities 74 that were made through openings 36, 37 of femoral drill guide 11 or left in the distal femur by the previous femoral component for the knee prosthesis.

Figure 14:
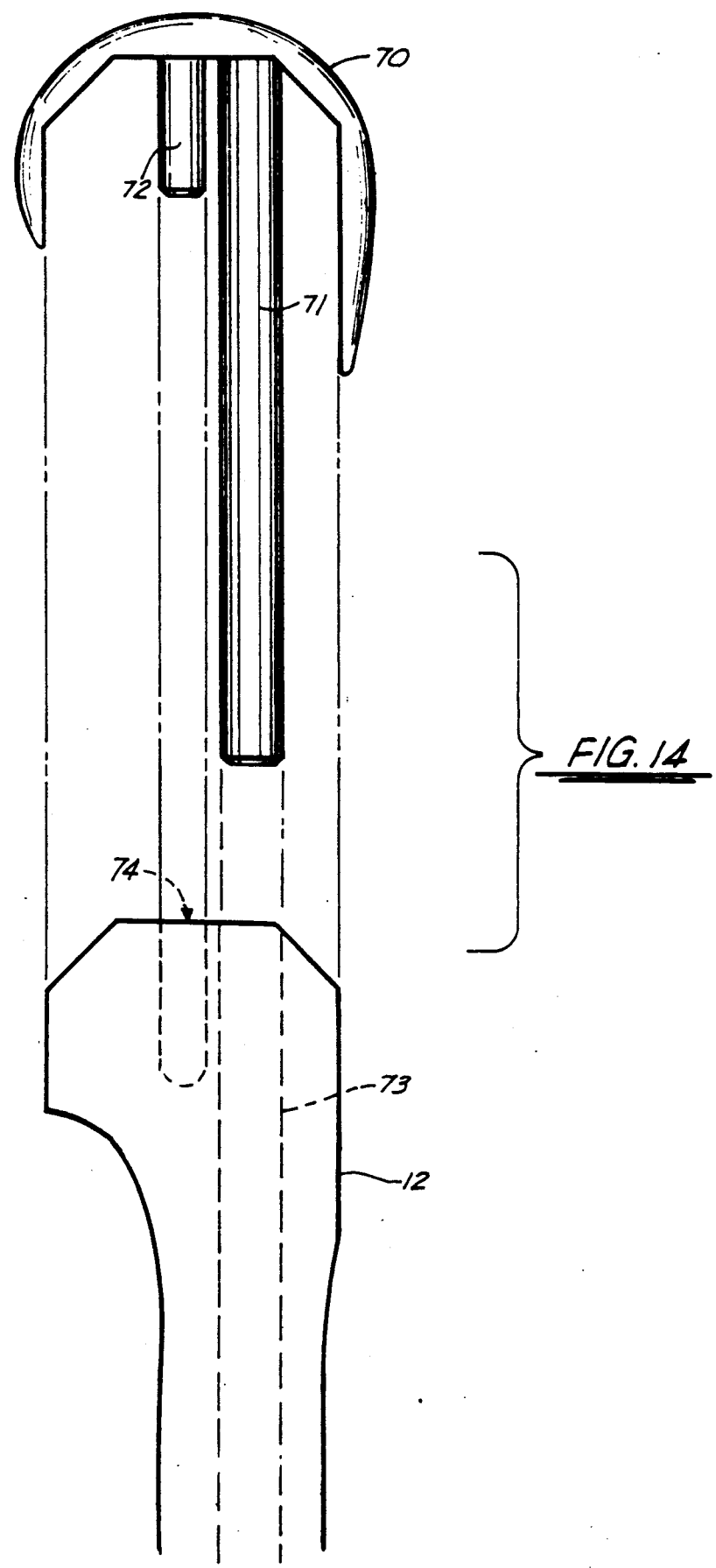
FIG. 14 is a schematic view of the distal femur after cutting and prior to the affixation of a long stemmed femoral component thereto.

In FIG. 14, the femur 12 is illustrated with the cuts having been made using cutting block 50 and prior to the installation of a new long stem component 70 that includes an elongated stem 71 and a pair of spaced apart pegs 72, the stem 71 registering in the opening 73 that has been formed in the intramedullary canal using drill/reamer 30. The pair of cavities 74 represents openings in the femur 12 for accommodating the pair of pegs 72.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A femoral instrumentation apparatus for long stem surgery comprising:

(a) an elongated femoral drill/reamer for placement in the intramedullary canal to define an anatomical axis of the intramedullary canal and opening for the femoral long stem;

(b) a femoral drill guide body having a flat lower surface adapted for placement during use upon the distal femur, a line normal to the flat lower surface defining a mechanical axis;

(c) a cylindrical drill guide opening through the guide body with a central axis that aligns with the drill-/reamer anatomical axis and forms an angle of between zero and twenty degrees (0°-20°) with the mechanical axis; and (d) a cutting block having a flat lower surface and an opening therethrough that corresponds to the drill guide opening so that the cutting block flat surface can be oriented upon the femur using the drill-/reamer after removal of the drill guide and without removal of the drill reamer to ensure that the drill guide and cutting block flat surfaces are correspondingly oriented.

2. The femoral instrumentation apparatus of claim 1 further comprising collet means removably attachable to the drill guide body for orienting the femoral drill guide using the drill/reamer, the collet means having a drill/reamer guide opening that conforms to the outer surface of the drill/reamer.

3. The femoral instrumentation apparatus of claim 2 further comprising a slot and the slot carries a pair of attachment posts, and the collet means removably attaches to the posts.

4. The femoral instrumentation apparatus of claim 1 wherein the drill guide body has a ledge intersecting the guide body with multiple openings therein for affixing the drill guide to the femur at the openings by using a fastener therethrough.

5. The femoral instrumentation apparatus of claim 4 wherein the cutting block means has multiple slots therein defining cutting guides, and a pair of intersecting portions, one of which is a ledge that corresponds to the ledge of the femoral drill guide body.

6. The femoral instrumentation apparatus of claim 5 wherein the cutting block has a rectangular body.

7. The femoral instrumentation apparatus of claim 6 wherein the rectangular body has a diagonal slot therethrough.

8. The femoral instrumentation of claim 5 wherein the cutting block has a ledge portion with an array of alignment openings thereon that correspond to the ledge openings of the drill guide so that the alignment openings of the drill guide ledge can be used to similarly place the cutting block ledge upon the femur using pins through the alignment openings.

9. The femoral instrumentation of claim 8 wherein the ledge of the cutting block means is removably attached to the cutting block means.

10. The femoral instrumentation apparatus of claim 9 wherein the ledge is bolted to the cutting block means using a removable bolted connection.

11. The femoral instrumentation apparatus of claim 9 wherein the ledge forms an anterior femoral ledge.

12. The femoral instrumentation apparatus of claim 5 wherein the cutting block means comprises a cutting block with a flat lower surface and having a drill guide opening therethrough for aligning the cutting block on the drill/reamer while it is placed in the intramedullary canal.

13. The femoral instrumentation apparatus of claim 12 wherein the opening comprises a pair of cylindrical bores that form acute angles with a line normal to the cutting block flat surface.

14. The femoral instrumentation apparatus of claim 13 wherein the cutting block has a pair of opposite flat surfaces, and the cylindrical bores intersect each of the flat surfaces at an acute angle.

15. The femoral instrumentation apparatus of claim 14 wherein the bores communicate with one another.

16. The femoral instrumentation apparatus of claim 5 wherein the cutting block means can be oriented upon the femur using the combination of the drill/reamer position, and the drill guide ledge position after the drill guide has been removed from the femur and drill-/reamer, and there is further provided corresponding alignment means on each of corresponding ledges of the drill guide and cutting block.

17. The femoral instrumentation apparatus of claim 1 wherein the collet means extends beyond the dimensions of the guide body.

18. The femoral instrumentation apparatus of claim 17 wherein the collet means is reversible in the slot, so that it can be placed in left or right positions.

19. A femoral instrumentation apparatus for long stem surgery comprising:
(a) an elongated femoral drill/reamer for placement in the intramedullary canal;
(b) a femoral drill guide body having a pair of intersecting flanges adapted for placement during use on the anterior ledge and anterior femoral cortex of the distal femur;
(c) a transverse slot across one of the flanges;
(d) an opening through one of the flanges and communicating with the slot;
(e) collet means removably attachable to the drill guide body at the slot for orienting the femoral drill guide using the drill/reamer, the collet means having a drill/reamer guide opening that conforms to the outer surface of the drill/reamer; and
(f) cutting block means having an opening therethrough receptive of the drill/reamer and a plurality of cutting guides for properly orienting cuts by first orienting the cutting block to the drill/reamer.

20. A method of femoral instrumentation and cutting for use in long stem surgery comprising the steps of:
a) placing on the distal femur a drill guide body having an angled opening therethrough and an anterior ledge;
b) placing the anterior ledge on the existing anterior femoral cortex;
c) selectively orienting the drill guide into a desired position with respect to medial/lateral and rotational orientation;
d) fixing the drill guide to the femur using a fastener;
e) inserting a drill/reamer through the opening of the drill guide and partially into the femur intramedullary canal;
f) removing the drill guide from the femur while maintaining a portion of the drill/reamer within the intramedullary canal;
g) placing a cutting block with an angled opening therein on the drill/reamer by attachment to the opening;
h) orienting the cutting block on the distal femur using the drill/reamer; and
i) cutting the distal femur using the placed and oriented cutting block.

21. The method of claim 20 wherein in step "a" the drill guide has a flat undersurface and the flat undersurface registers upon the distal femur.

22. The method of claim 21 wherein in step "a" the drill guide opening is cylindrical and in step "e" the drill/reamer forms an angle with the flat undersurface of between seventy degrees and ninety degrees (70°–90°).

23. The method of claim 22 wherein in step "a" the opening in the drill guide has an inner diameter sized to snugly fit the outer diameter of the drill/reamer used in step "e".

24. The method of claim 23 wherein in step "g" the cutting block has a flat underside surface.

25. The method of claim 24 wherein in step "i" the cuts include diagonal cuts with respect to the flat underside surface of the cutting block.

* * * * *